(12) United States Patent
Lee

(10) Patent No.: US 9,131,916 B2
(45) Date of Patent: Sep. 15, 2015

(54) RADIATION IMAGING APPARATUS AND CONTROL METHOD THEREOF

(71) Applicant: Samsung Electronics Co., Ltd., Gyeonggi-do (KR)

(72) Inventor: Woong Lee, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 30 days.

(21) Appl. No.: 13/955,434

(22) Filed: Jul. 31, 2013

(65) Prior Publication Data

US 2014/0126699 A1 May 8, 2014

(30) Foreign Application Priority Data

Nov. 6, 2012 (KR) .......................... 10-2012-0124564

(51) Int. Cl.
*G01N 23/04* (2006.01)
*A61B 6/00* (2006.01)
*A61B 6/03* (2006.01)
*A61B 5/107* (2006.01)
*A61B 6/04* (2006.01)

(52) U.S. Cl.
CPC .................. *A61B 6/544* (2013.01); *A61B 6/032* (2013.01); *A61B 5/1072* (2013.01); *A61B 5/1079* (2013.01); *A61B 6/0407* (2013.01)

(58) Field of Classification Search
CPC ........ A61B 6/032; A61B 5/107; A61B 6/5247; A61B 5/1072; A61B 5/1079; A61B 6/542
USPC ....................................... 378/4, 15, 19, 62, 63
See application file for complete search history.

(56) References Cited

U.S. PATENT DOCUMENTS

| 7,551,711 B2 * | 6/2009 | Sarment et al. ................. 378/15 |
| 2005/0031082 A1 | 2/2005 | Haaga et al. |
| 2007/0206725 A1 | 9/2007 | Vogtmeier et al. |
| 2011/0194670 A1 | 8/2011 | Borghese et al. |

FOREIGN PATENT DOCUMENTS

| DE | 101 18 183 A1 | 11/2002 |
| DE | 10 2005 028 415 A1 | 12/2006 |
| JP | 2002-355243 A | 12/2002 |
| JP | 2003-061947 A | 3/2003 |
| JP | 2011-143239 A | 7/2011 |
| KR | 10-0702148 B1 | 3/2007 |
| KR | 10-0962787 B1 | 6/2010 |

* cited by examiner

*Primary Examiner* — Courtney Thomas
(74) *Attorney, Agent, or Firm* — Cha & Reiter, LLC

(57) ABSTRACT

A radiation imaging apparatus has a camera installed on a gantry, and a method creates volume data of a subject through images of the subject photographed by the camera and calculates an optimum dose of radiation based on the volume data of the subject. The radiation imaging apparatus includes the gantry, and the camera installed on the gantry to photograph a subject.

20 Claims, 14 Drawing Sheets

RADIATION IMAGING APPARATUS AND CONTROL METHOD THEREOF

CLAIM OF PRIORITY

This application claims, pursuant to 35 USC 119(a), priority to and the benefit of the earlier filing date of Korean Patent Application No. 2012-0124564, filed on Nov. 6, 2012 in the Korean Intellectual Property Office, the entire disclosure of which is incorporated herein by reference.

BACKGROUND

1. Field of the Invention

The present disclosure relates to a radiation imaging apparatus for irradiating X-rays to a subject, and more particularly to reconstructing signals of X-rays which have passed through the subject using a computer to create images of the subject, and a control method thereof.

2. Description of the Related Art

An X-ray imaging apparatus is an apparatus for irradiating X-rays to a subject and analyzing X-rays which have passed through the subject to measure the internal structure of the subject. Since various tissues constituting a subject have different degrees of X-ray radiolucency, the internal structure of the subject can be imaged using attenuation coefficients obtained by quantifying different degrees of X-ray radiolucency.

The X-ray imaging apparatus can be classified into a general X-ray system for irradiating X-rays in one direction, and a computed tomography (CT) system for irradiating X-rays in many directions and reconstructing images using a computer.

Unlike magnetic resonance imaging (MRI) systems or ultrasonic systems, the CT system uses radiation such as X-rays. Radiation does harm to a human body. In particular, if a high dose of radiation is emitted to a human body so that the human body is excessively exposed to the radiation, the damage will be significant.

Accordingly, a technology is needed for scanning a subject by irradiating a minimum dose of radiation with which images of the subject can be acquired.

SUMMARY

Therefore, it is an aspect of the present invention to provide a radiation imaging apparatus with a camera installed on a gantry, the radiation imaging apparatus configured to create volume data of a subject photographed by the camera through images of the subject, and to calculate an optimum dose of radiation based on the volume data of the subject.

Additional aspects of the invention will be set forth in part in the description which follows and, in part, will be obvious from the description, or may be learned by practice of the invention.

In accordance with one aspect of the present invention, a radiation imaging apparatus includes: a gantry; and a camera installed on the gantry, and configured to photograph a subject.

The radiation imaging apparatus may further include a controller configured to rotate the gantry, and to drive the camera to photograph the subject while the gantry rotates.

The controller may control driving of the camera to photograph the subject at predetermined regular time intervals while the gantry rotates.

The controller may control driving of the camera to photograph the subject at predetermined regular angles while the gantry rotates.

The controller may create volume data of the subject from images of the subject acquired from the camera while the gantry rotates.

The controller may calculate an optimum dose of radiation based on volume data of a scan zone of the subject.

The controller may divide a volume of the subject into a plurality of volumes in a direction perpendicular to the driving axis of the gantry, obtain the center line of each divided volume, and adjust the position of the center line of a divided volume including a scan zone of the subject such that the center line of the divided volume matches the driving axis of the gantry.

The controller may obtain the center line of each divided volume by connecting the center points of slices constituting the volume to each other.

The radiation imaging apparatus may further include a tiltable cradle, wherein the controller adjusts tilting of the cradle such that the center line of the volume including the scan zone of the subject matches the driving axis of the gantry.

A plurality of cameras may be installed on the gantry at predetermined regular distance or angular intervals.

The radiation imaging apparatus may further include a controller configured to create volume data of the subject from images of the subject acquired by the plurality of cameras.

The camera may include an infrared camera.

In accordance with another aspect of the present invention, a control method of a radiation imaging apparatus includes: at a camera installed on a gantry, photographing a subject; creating volume data of the subject from images of the subject acquired by the camera; and calculating an optimum dose of radiation that is to be irradiated to a scan zone of the subject, based on the volume data of the subject.

The photographing of the subject may include: rotating the gantry; and driving the camera to photograph the subject while the gantry rotates.

The driving of the camera to photograph the subject while the gantry rotates may include controlling driving of the camera to photograph the subject at predetermined time intervals while the gantry rotates.

The driving of the camera to photograph the subject while the gantry rotates may include controlling driving of the camera to photograph the subject at predetermined angles while the gantry rotates.

The calculating of the optimum dose of radiation that is to be irradiated to the scan zone of the subject, based on the volume data of the subject, may include: dividing the volume of the subject into a plurality of volumes; obtaining the center line of each divided volume; adjusting the position of the center line of a divided volume including the scan zone of the subject such that the center line of the volume matches the driving axis of the gantry; and calculating an optimum dose of radiation based on the volume including the scan zone of the subject.

The dividing of the volume of the subject into the plurality of volumes may include dividing the volume of the subject into the plurality of volumes in a direction perpendicular to the driving axis of the gantry.

The obtaining of the center line of each divided volume may include:
obtaining the center points of slices configuring the volume; and obtaining the center line of the volume by connecting the center points of the slices to each other.

The adjusting of the position of the center line of the volume including the scan zone of the subject, such that the center line of the volume matches the driving axis of the gantry, may include adjusting tilting of a tiltable cradle on which the subject lies such that the center line of the volume including the scan zone of the subject matches the driving axis of the gantry.

According to an exemplary embodiment, by adjusting a dose of radiation based on volume data of a subject, it is possible to prevent the subject from being exposed to an unnecessarily high dose of radiation.

Also, by scanning a subject after adjusting the position of the center line of the subject such that the center line of the subject matches the driving axis of a gantry, it is possible to prevent the subject from being exposed to a unnecessarily high dose of radiation, while acquiring high quality of images.

BRIEF DESCRIPTION OF THE DRAWINGS

These and/or other aspects of the invention will become apparent and more readily appreciated from the following description of the exemplary embodiments, taken in conjunction with the accompanying drawings of which.

DETAILED DESCRIPTION

Figure 1:
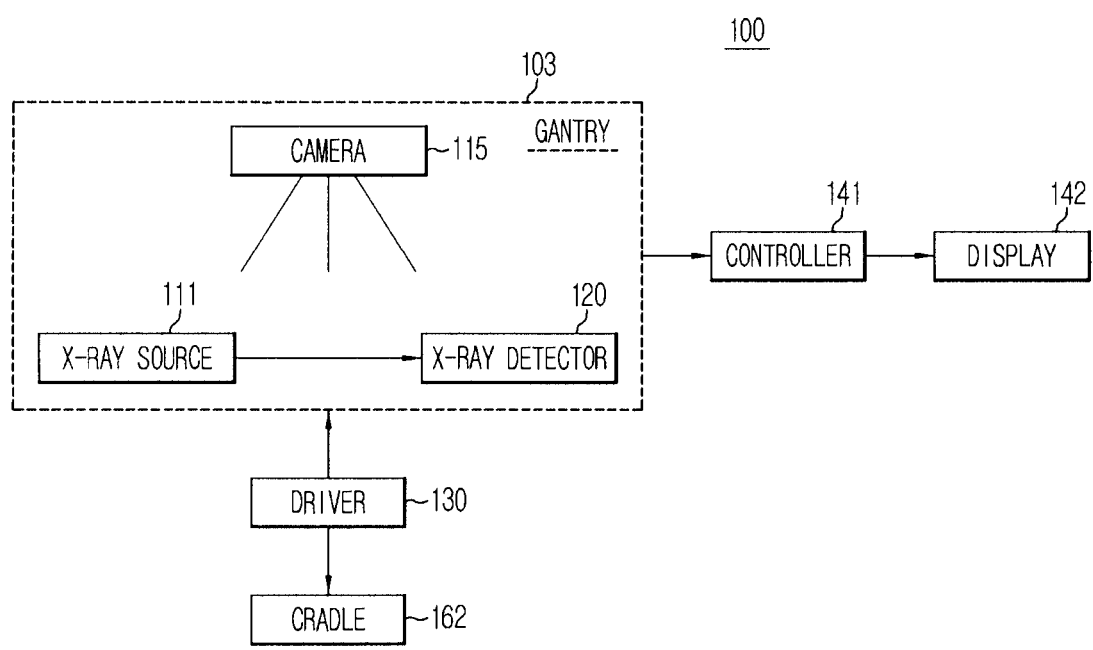
FIG. 1 is a block diagram showing a computed tomography (CT) apparatus in accordance with an exemplary embodiment of the present invention.

Reference will now be made in detail to the exemplary embodiments of the present invention, examples of which are illustrated in the accompanying drawings, wherein like reference numerals refer to like elements throughout. In the following description, a detailed explanation of known related functions and constructions may be omitted to avoid unnecessarily obscuring the subject matter of the present invention. The present invention may, however, be embodied in many different forms and should not be construed as limited to the exemplary embodiments set forth herein. In addition, terms described herein, which are defined with reference to the functions of the present invention, may be implemented differently depending on a user or operator's intention and practice. Therefore, the terms should be understood on the basis of the disclosure throughout the specification. The principles and features of the present invention may be employed in varied and numerous exemplary embodiments without departing from the scope of the present invention.

Furthermore, although the drawings represent exemplary embodiments of the present invention, the drawings are not necessarily to scale and certain features may be exaggerated or omitted in order to more clearly illustrate and explain the present invention.

Hereinafter, a radiation imaging apparatus in accordance with an exemplary embodiment of the present invention will be described in detail with reference to the appended drawings.

Radiation refers herein to energy in the form of particles or electromagnetic waves, which may be emitted, for example, when unstable radionuclides are converted into relatively stable nuclides. Representative examples of radiation include X-rays, alpha rays, beta rays, gamma rays, neutron rays, infrared rays, visible rays, etc. In an exemplary embodiment which will be described later, for convenience of description, radiation refers herein to X-rays; however, the radiation is not limited to X-rays.

Meanwhile, X-ray imaging apparatuses for creating an image of an internal portion of a subject using X-rays are classified into a general X-ray system, a dental X-ray system for examining the oral cavity, a mammographic system for examining the human breast, etc. according to the targets to be scanned, and also may be classified into a general X-ray system that scans a subject at one angle and a tomography system that scans a subject at many angles and combines the scanned images into an overall image, according to the scanning angles. In the following exemplary embodiment, for convenience of description, a computed tomography (CT) apparatus is used as an example.

Figure 2:
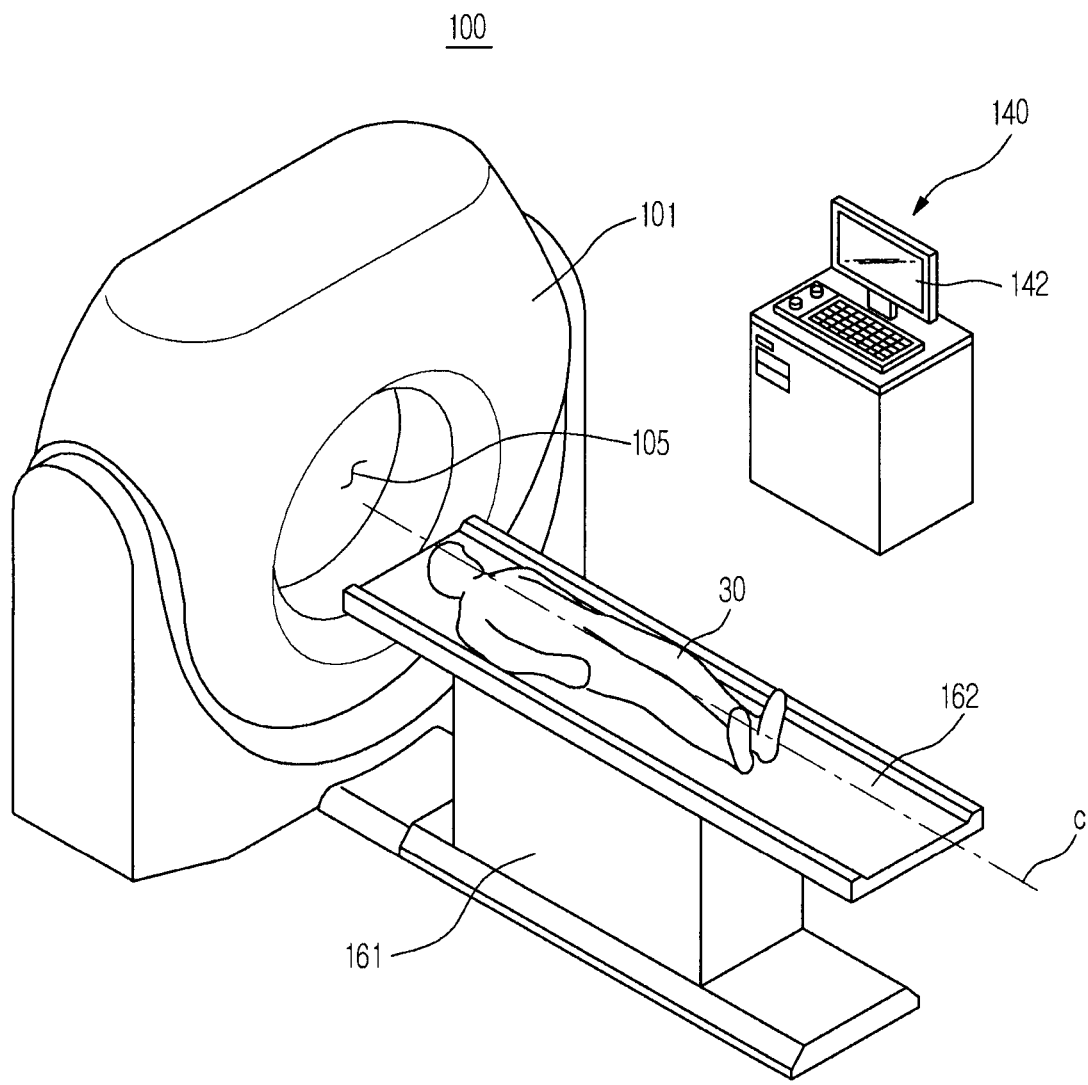
FIG. 2 shows the configuration of the CT apparatus of FIG. 1.
Figure 3:
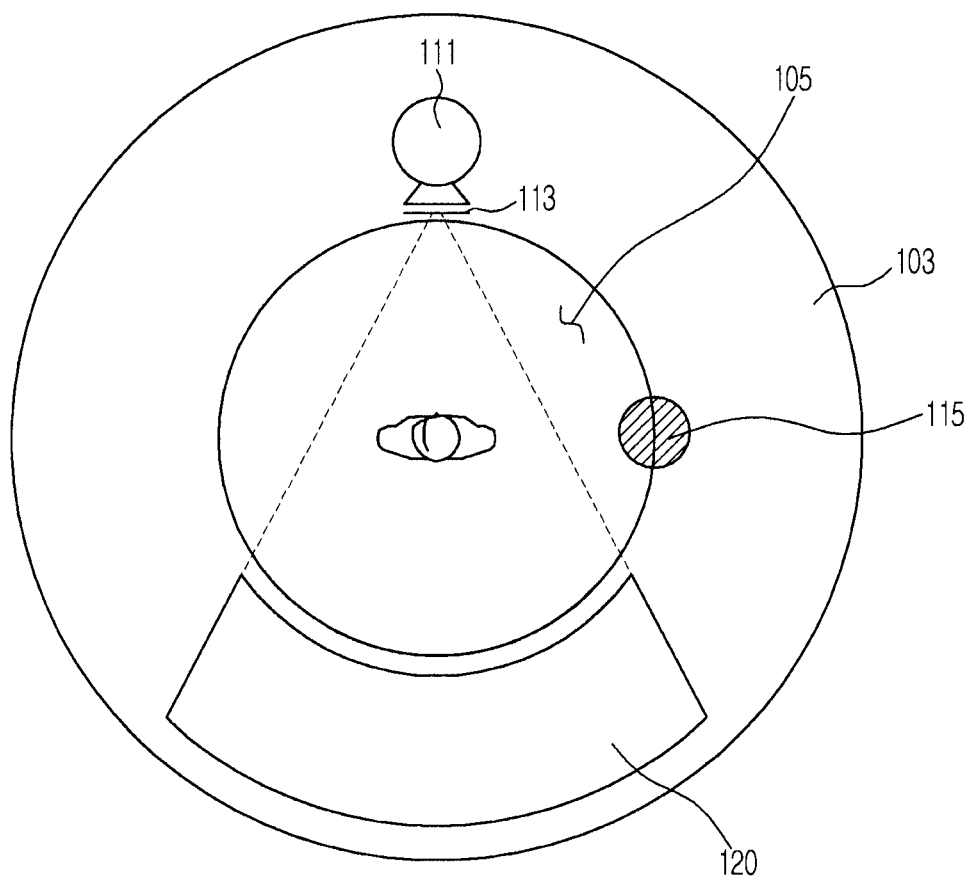
FIG. 3 is a cross-sectional view of a gantry of the CT apparatus of FIG. 2.

FIG. 1 is a block diagram showing a CT apparatus 100 in accordance with the exemplary embodiment of the present invention, FIG. 2 shows the configuration of the CT apparatus of FIG. 1, and FIG. 3 is a cross-sectional view of a gantry of the CT apparatus of FIG. 2.

Hereinafter, the structure and operation of the CT apparatus 100 will be described with reference to FIGS. 1, 2, and 3.

Referring to FIGS. 1-3, the CT apparatus 100 includes a X-ray source 111 for generating X-rays and irradiating the X-rays to a subject 30, a X-ray detector 120 for detecting X-rays which have passed through the subject 30 to acquire X-ray data, a camera 115 for photographing the subject 30, a controller 141 for acquiring volume data of the subject 30 from images of the subject 30 photographed by the camera 115 and reconstructing the X-ray data acquired by the X-ray detector 120 to create an image of the subject 30, a driver 130 for driving a gantry 103 and a cradle 162, and a display 142 for displaying the image of the subject 30 and/or for displaying an optimum dose of radiation, as described herein.

The X-ray source 111 and the X-ray detector 120 are installed on the gantry 103 to irradiate X-rays to the subject 30 and detect X-rays which have passed through the subject 30, while rotating around the subject 30 within a predetermined angular range according to rotation of the gantry 103.

The X-ray source 111 includes an X-ray tube for generating X-rays, and receives power from an external power supply to generate X-rays. If a high voltage is applied to the anode and cathode of the X-ray tube, thermoelectrons are accelerated and collide with target materials of the anode to generate X-rays. A generator for generating the high voltage may be installed on the gantry 103 or provided outside the gantry 103.

Meanwhile, the energy of X-rays may be adjusted by a tube voltage that is supplied to the X-ray source 111, for example, by the controller 141, and the intensity or dose of the X-rays may be adjusted by tube current and an exposure time, for example, by the controller 141. The energy of the X-rays, and the intensity or dose of the X-rays may be determined according to the kind, thickness, or diagnosis purpose of the subject 30 or a portion of the subject to receive the X-rays.

The X-ray source 111 may irradiate monochromatic X-rays or polychromatic X-rays. If the X-ray sources 111 may irradiate polychromatic X-rays having a specific energy band, the energy band of the irradiated X-rays may be defined by upper and lower limits.

The upper limit of the energy band, that is, the maximum energy of the irradiated X-rays may be adjusted according to the magnitude of the tube voltage or adjusted by a filter, and the lower limit of the energy band, that is, the minimum energy of the irradiated X-rays may be adjusted by a filter. The filter functions to pass or filter only a specific energy band of X-rays therethrough. If the X-ray source 111 includes a filter for filtering out a low energy band of X-rays, it is possible to increase the lower limit of an energy band, thus raising an average energy of irradiated X-rays.

The X-ray detector 120 includes a plurality of detection modules arranged in the form of an array having a predetermined shape or configuration of the detection modules. Each detection module detects X-rays which have passed through the subject 30, converts the detected X-rays into electrical signals to acquire digital X-ray data, and transmits the digital X-ray data to the controller 141.

As shown in FIG. 3, the camera 115 is installed on the gantry 103 in order to photograph the subject 30 prior to X-raying the subject 30. The camera 115 photographs the subject 30 before scanning the subject 30, and transmits images photographed by the camera 115 to the controller 141, and the controller 141 acquires volume data of the subject 30 using the images.

The camera 115 may be an infrared camera, but the camera 115 may be an arbitrary camera capable of photographing the subject 30 to acquire digital information of the subject 30.

The controller 141 reconstructs an image using the digital X-ray data transmitted from the X-ray detector 120. A method of reconstructing an image may include an iterative method, a direct Fourier method, a filtered back projection method, etc. The image reconstructed by the controller 141 is output through the display 142; for example, to be displayed to a user such as a doctor, an X-ray technician, etc.

Also, the controller 141 may create volume data of the subject 30 using images of the subject 30 photographed by the camera 115. The controller 141 may create three-dimensional (3D) volume data of the subject 30 from images photographed by the camera 115 through multi-view 3D reconstruction methods known in the art. Alternatively, if the camera 141 is an infrared camera, the controller 141 measures a distance to the subject 30 based on infrared rays reflected from the subject 30, and creates a depth map using the distance to the subject 30, thereby creating volume data of the subject 30.

Operation of creating the volume data of the subject 30 using the images of the subject 30 photographed by the camera 115, and operation of calculating an optimum dose of radiation using the volume data of the subject 30 will be described later.

The driver 130 includes a driving motor for driving the gantry 103, and a driving motor for driving the cradle 162; for example, to move the subject 30 into or out of the bore 105 of the housing 101, as shown in FIGS. 2-3, and the controller 141 may control the driver 130 to control rotation of the gantry 103 and movement of the cradle 162. Also, the cradle 162 is configured to be tiltable, which will be described with reference to FIG. 13, later.

Referring to FIGS. 2 and 3, the CT apparatus 100 includes the X-ray source 111, the X-ray detector 120, and the camera 115 therein, and further includes the housing 101 supporting the components, the cradle 162 for transporting the subject 30 lying or positioned thereon, a cradle table 161 supporting the cradle 162, and a workstation 140 for displaying an image of the subject 30 and receiving control commands for controlling the entire operation of the CT apparatus 100 from a user.

The workstation 140 includes the display unit 142, and the controller 141 described above may be included in the workstation 140. As shown in FIG. 3, the workstation 140 may include a keyboard or other input devices for receiving user commands. For example, the display unit 142 may include a touch screen for displaying a graphic user interface (GUI) for touch input of user commands.

The gantry 103 may be included in the housing 101, and the X-ray source 111, the X-ray detector 120, and the camera 115 are installed on the gantry 103. If the subject 30 lies or is positioned on the cradle 162, the driver 130 transports the cradle 162 into or out of a bore 105 formed in the center area of the housing 101, and at this time, the subject 30 lying or positioned on the cradle 162 is transported together with the cradle 162. The controller 141 controls the driver 130 to adjust the transportation distance of the cradle 162 such that an examination zone (that is, a scan zone) of the subject 30 is located within the bore 105.

The X-ray source 111 and the X-ray detector 120 in the gantry 103 are fixed to face each other, as shown in FIG. 3, so that X-rays irradiated from the X-ray source 111 can be detected by the X-ray detector 120. When CT scanning starts, the driver 130 provides rotational power to the gantry 103, and if X-rays are irradiated from the X-ray source 110 to the subject 30 while the gantry 103 rotates around the bore 105, the X-ray detector 120 detects X-rays which have passed through the subject 30. The controller 141 may control the rotation speed and revolutions per minute (rpm) of the gantry 103 through the driver 130.

Meanwhile, a collimator 113 may be disposed at the front or at a section of the X-ray source 111 that irradiates X-rays, and the collimator 113 may adjust the width or cross-sectional area of an X-ray beam irradiated from the X-ray source 111. Accordingly, the collimator 113 decreases scattering rays in different directions to reduce a computed tomography dose index (CTDI) with respect to the subject 30. In an alternative exemplary embodiment, another collimator may be disposed in front of or at a receiving section of the X-ray detector 120 so that X-rays only from an area-of-interest are detected. The collimator disposed in front of or at the receiving section of the X-ray detector 120 may eliminate scattering rays, and adjust the width or cross-sectional area of an X-ray beam which passed through the subject 30 to determine the thickness of a slice of a volume of the subject 30.

Figure 4:
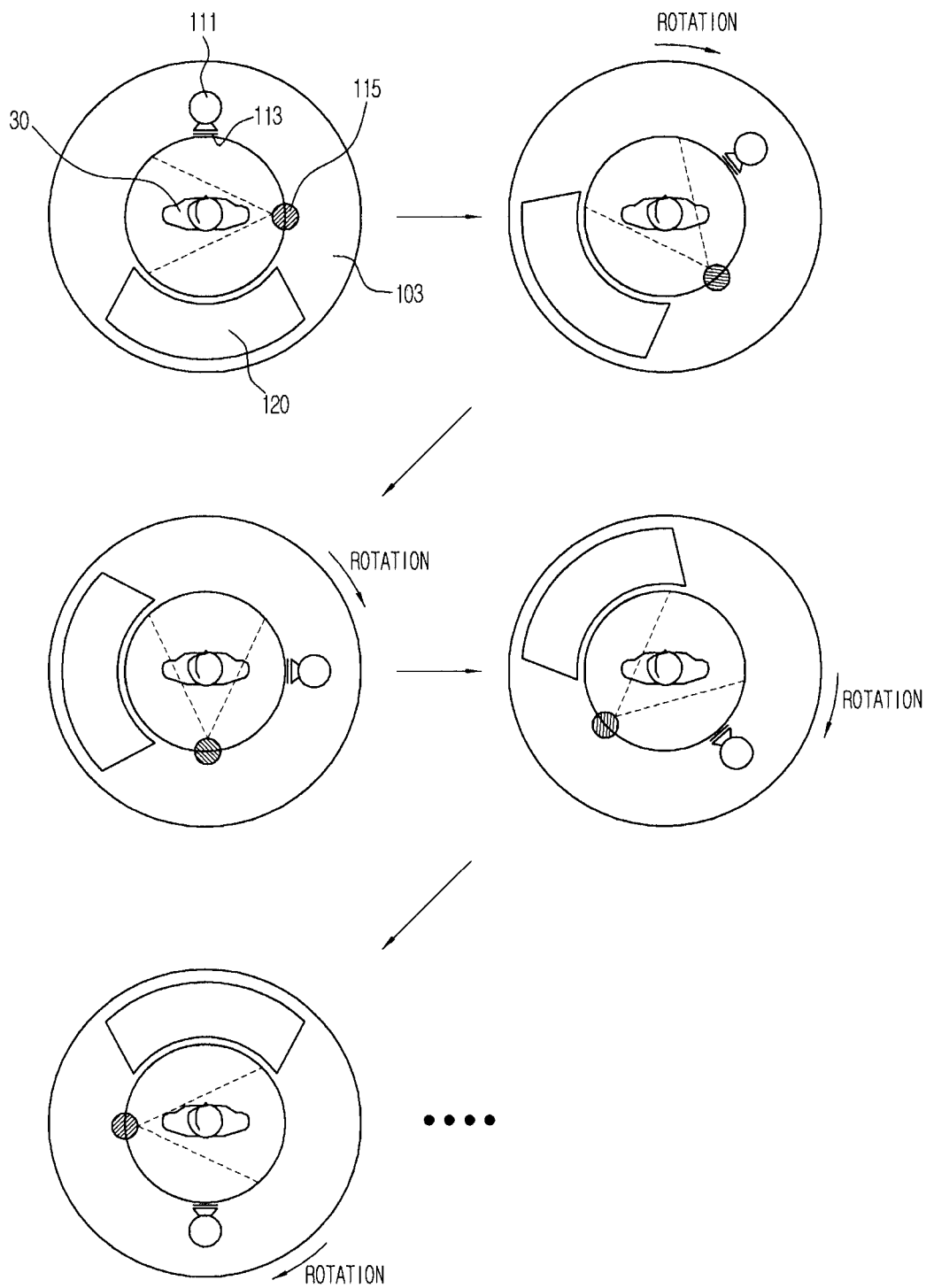
FIG. 4 shows an example in which a camera installed on the gantry shown in FIG. 3 photographs a subject while the gantry rotates.
Figure 5:
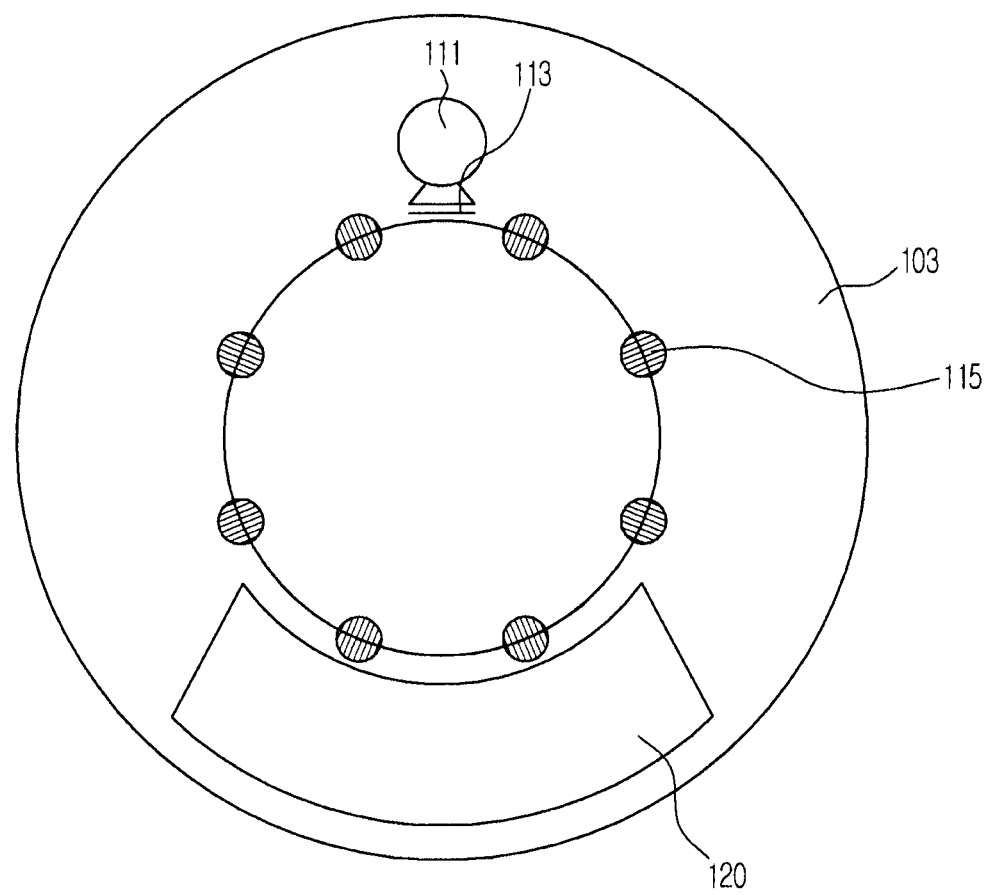
FIG. 5 is a cross-sectional view of a gantry of the CT apparatus in accordance with an alternative exemplary embodiment of the present invention.
Figure 6:
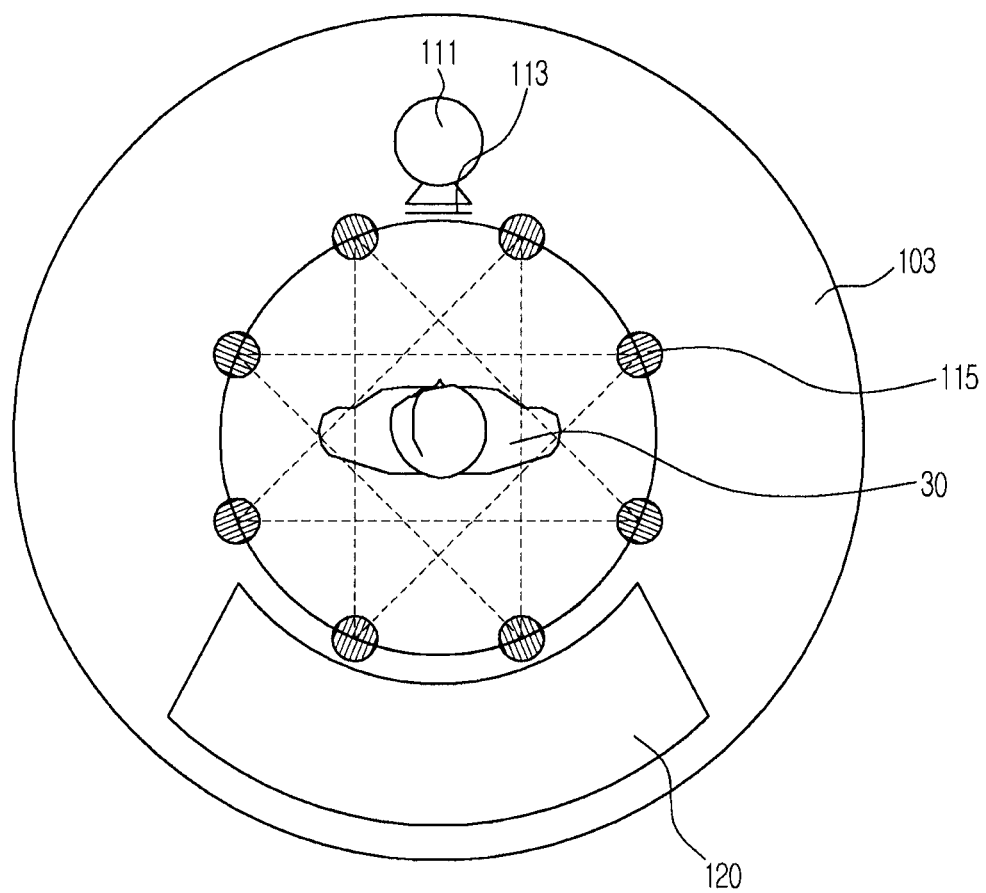
FIG. 6 shows an example in which a plurality of cameras installed on the gantry of FIG. 5 photograph a subject.

FIG. 4 shows an example in which the camera 115, installed on the gantry 103 shown in FIG. 3, scans the subject 30 while the gantry 103 rotates, FIG. 5 is a cross-sectional view of the gantry 103 of the CT apparatus 100 in accordance with an alternative exemplary embodiment of the present invention, and FIG. 6 shows an example in which a plurality of cameras 115 installed on the gantry 103 of FIG. 5 scan a subject 30.

A single camera 115 may be installed on the gantry 103, as shown in FIGS. 3 and 4.

As such, if a single camera 115 is installed, the controller 141 in FIG. 1 controls driving of the camera 115 such that the camera 115 photographs the subject 30 at predetermined regular time intervals or at predetermined regular angles while the gantry 103 rotates around the subject 30, as shown in FIG. 4, for example, at every rotation of 45°.

Since the camera 115 photographs the subject 30 at predetermined regular time intervals or at predetermined regular angles while the gantry 103 rotates around the subject 30, images of the subject 30 photographed at multiple angles may be acquired.

FIG. 4 shows operation in which, while the gantry 103 rotates by 180° in a clockwise direction relative to the views of the gantry 103 shown in FIG. 4, the camera 115 photographs the subject 30 at positions of 0°, 45°, 90°, 135°, and 180°. Rotation from 180° to 360° is symmetrical to the 180° rotation shown in FIG. 4, and accordingly, a detailed view thereof is omitted.

The installation location, photographing times, or photographing angles of the camera 115 as shown in FIG. 4 are only exemplary. That is, the camera 115 may installed at another location on the gantry 103, and also the camera 115 may photograph the subject 30 at different angles.

Images of the subject 30 acquired by photographing the subject 30 at predetermined regular time intervals or at predetermined regular angles while the gantry 103 rotates are images showing different sides of the subject 30 photographed at different angles, and the images are used for the controller 141 to construct 3D volume data of the subject 30.

As shown in FIG. 4, when a single camera 115 is installed on the gantry 103, the gantry 103 needs to be rotated to acquire images of the subject 30 photographed at different angles. In an alternative embodiment, as shown in FIG. 5, if a plurality of cameras 115 are installed on the gantry 103, images of the subject 30 photographed at different angles may be acquired without rotation of the gantry 103.

The number of the cameras 115 may be determined, for example, at the time of manufacture of the gantry 103, as a minimum number of cameras 115 capable of photographing images required for creating 3D volume data of the subject 30 without rotation of the gantry 103, and the locations at which the cameras 115 are installed may also be determined as locations at which images required for creating 3D volume data of the subject 30 can be photographed without rotation of the gantry 103. If the minimum number of cameras 115 or more are provided, it is possible to acquire images of the subject 30 photographed at different angles without rotation of the gantry 103.

If cameras less than the minimum number of cameras 115 are installed, the gantry 103 may be required to be rotated within a predetermined angle range. In this case, the predetermined rotation angle range of the gantry 103 may be smaller than the rotation angle range of the gantry 103 when a single camera 115 is installed. Alternatively, the creation of 3D volume data using fewer than a minimum number of cameras 115, or with cameras 115 positioned at irregular locations or angular intervals may be performed using imaging and 3D volume data processing methods known in the art.

FIG. 5 shows a state in which a plurality of cameras 115 have been installed on the gantry 103 so that images of a subject photographed at different angles can be acquired without rotation of the gantry 103. However, the number or locations of the cameras 115 shown in FIG. 5 are only exemplary. That is, a different number of cameras 115 may be arranged at different positions.

FIG. 6 shows an example in which the plurality of cameras 115, for example, eight camera regularly spaces at, for example, 45° around the drive axis c of the gantry 103, photograph a subject 30 without rotation of the gantry 103.

FIG. 4 shows an example in which the camera 115 photographs the subject 30 several times while the gantry 103 rotates around the subject 30 to acquire images of the subject 30 photographed at different angles. In the alternative embodiment in which a plurality of cameras 115 are installed as shown in FIG. 5, the individual cameras 115 photograph the subject 30 one time without having to rotate the gantry 103, thereby acquiring images of the subject 30 photographed at different angles, as shown in FIG. 6.

In this way, if the cameras 115 acquire two-dimensional (2D) image data of the subject 30 photographed at different angles, the controller 141 receives the 2D image data of the subject 30 to create 3D volume data of the subject 30, using image and 3D volume data processing methods known in the art.

Figure 7:
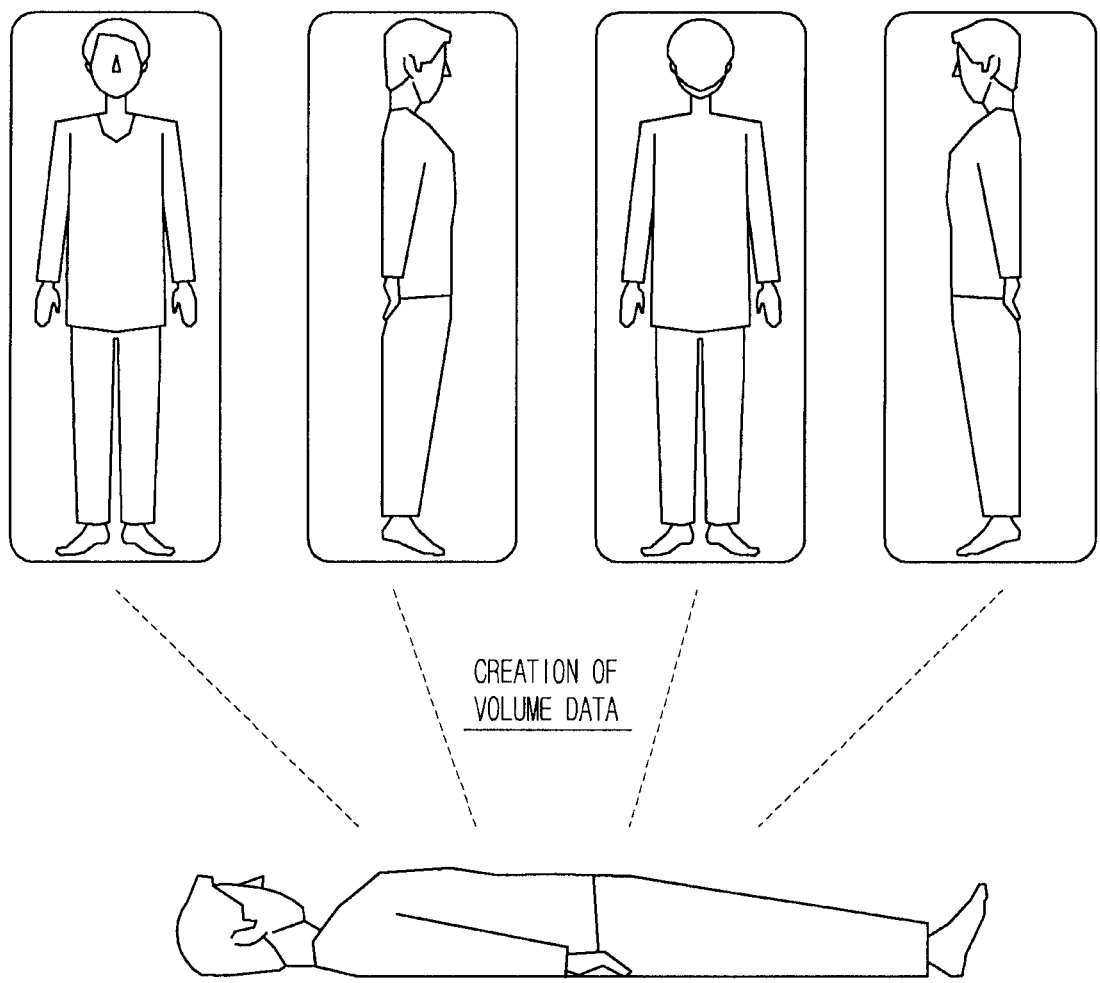
FIG. 7 shows an example in which volume data of the subject is acquired from images of the subject acquired by the cameras installed on the gantry.

FIG. 7 shows images of the subject 30 acquired when the cameras 115 have photographed the subject 30 at different angles, and the 3D volume data of the subject 30 is created based on the images of the subject 30.

The controller 141 may create the 3D volume data of the subject 30 from the images photographed by the cameras 115 through multi-view 3D reconstruction methods known in the art. Alternatively, if the camera 141 is an infrared camera, the controller 141 measures a distance to the subject 30 based on infrared rays reflected from the subject 30, and creates a depth map using the distance to the subject 30, thereby creating volume data of the subject 30.

After the volume data of the subject 30 is created, the controller 141 calculates an optimum dose of X-rays required for scanning the subject 30, based on volume data of a part including a scan zone of the subject 30.

At this time, if an optimum dose of X-rays is determined based on body measurement information, such as height or weight, without taking into account a somatotype or other physical characteristics of the subject 30 or portions thereof, a higher dose of X-rays than an optimal dose required for scanning may be irradiated.

However, if an optimum dose of X-rays is calculated using volume data including depth information or volume information of a part including a scan zone of the subject 30, it is possible to prevent the subject 30 from being exposed to an unnecessarily high dose of X-rays, compared to when an irradiation dose of X-rays is determined using only body measurement information, such as height or weight, without taking into account the somatotype of the subject 30.

Figure 11:
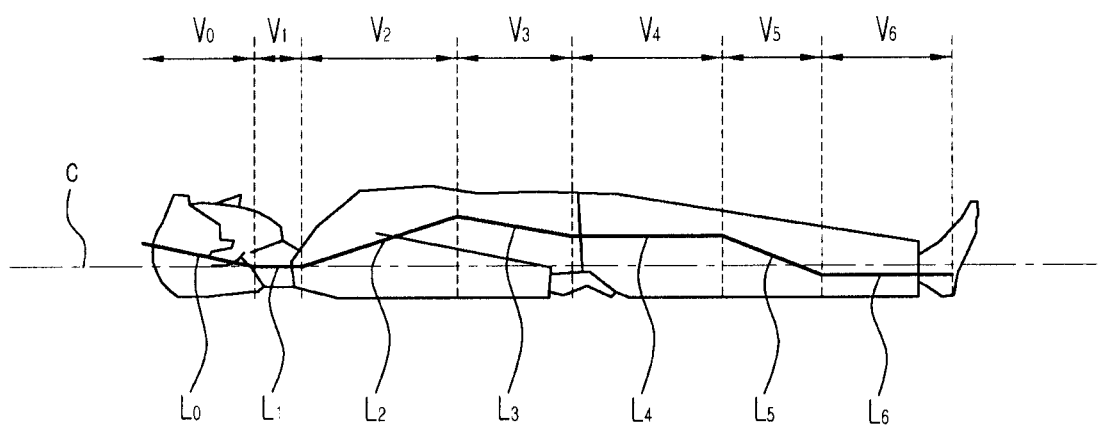
FIG. 11 shows the center lines of the individual volumes shown in FIG. 9 and the driving axis of the gantry.
Figure 12:
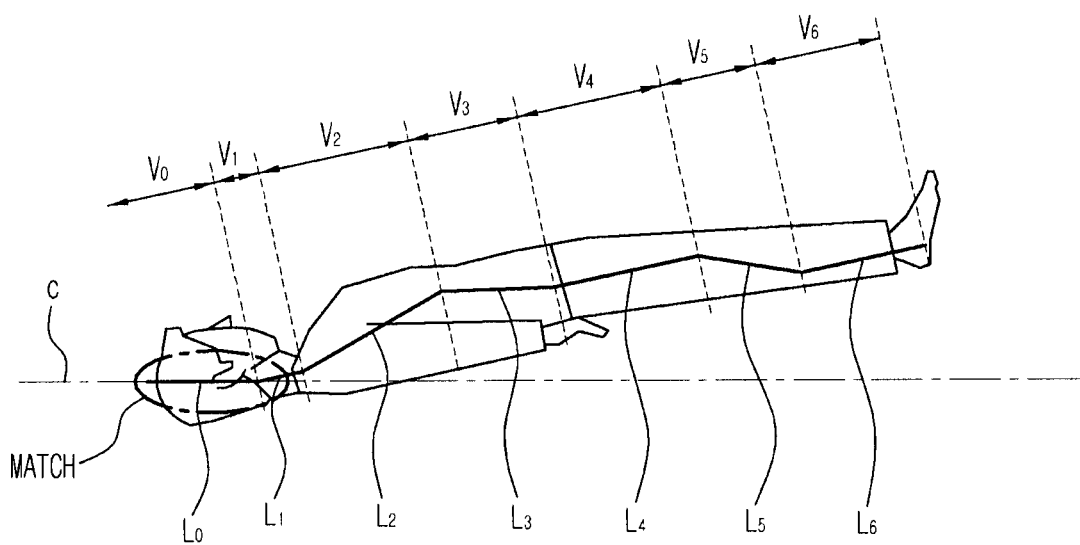
FIG. 12 shows an example in which one of the center lines of the volumes shown in FIG. 9 has matched the driving axis of the gantry.

Meanwhile, according to a study in the prior art, the CTDI increases when the center line of a subject deviates away from the center axis of a gantry, that is, the driving axis c of a gantry, shown in FIGS. 11-12. The prior art study shows that if the center of a subject is located about 30 mm. away from the driving axis of a gantry, the CTDI increases by 12% to 18%, and if the center of a subject is located about 60 mm. away from the driving axis of a gantry, the CTDI increases by 41% to 49%. Accordingly, the present invention reduces the CTDI and unnecessary exposure of the subject 30 to radiation by scanning the subject 30 after causing the driving axis c of the gantry 103, shown in FIGS. 11-12, to match the center line of the subject 30.

Hereinafter, a method of causing the driving axis c of the gantry 103 to match the center line of the subject 30 based on volume data of the subject 30 will be described in detail with reference to FIGS. 8 through 13.

Figure 8:
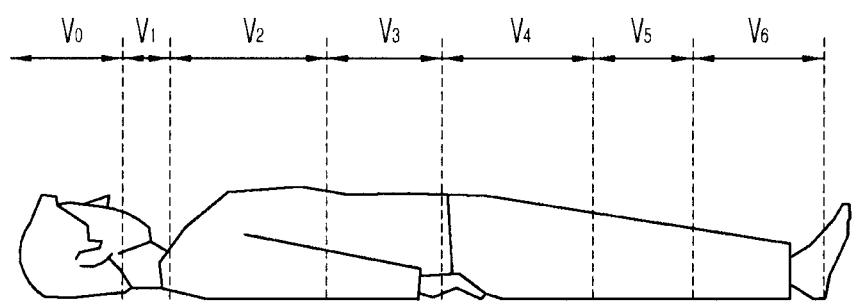
FIG. 8 shows an example in which a volume image created from the volume data of the subject is divided into a plurality of volumes.
Figure 9:
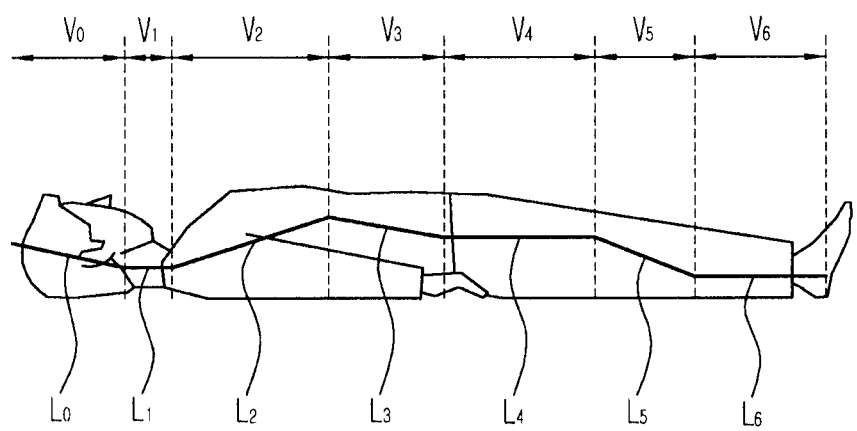
FIG. 9 shows the center lines of the individual volumes shown in FIG. 8.
Figure 10:
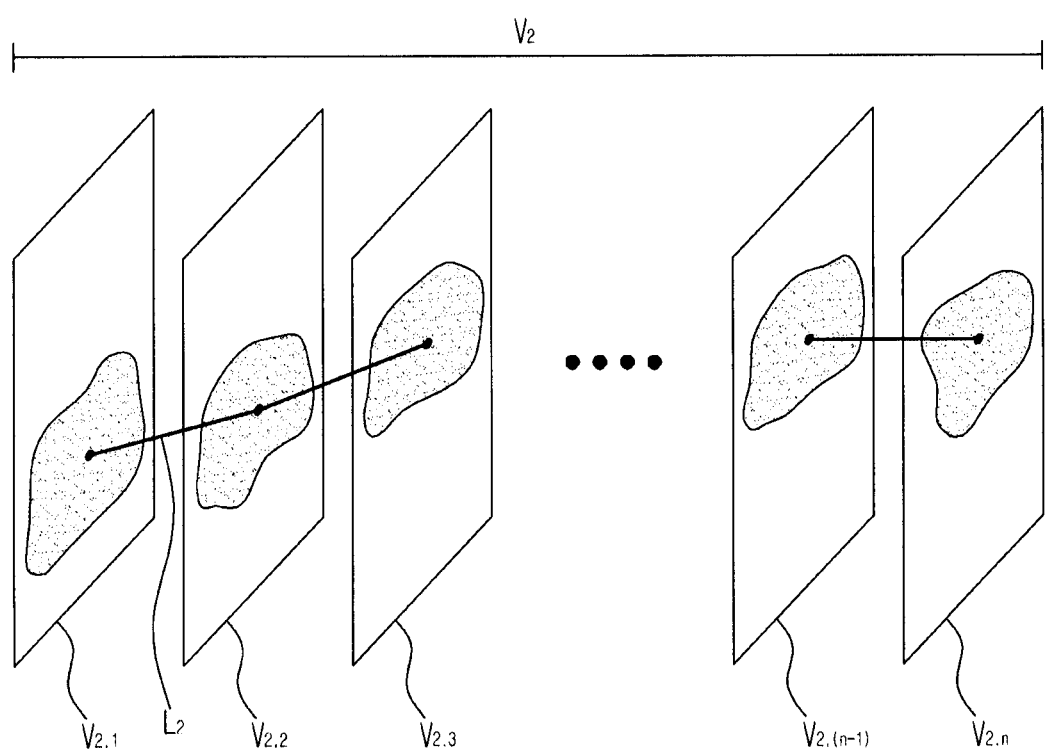
FIG. 10 shows a method of forming the center line of each volume shown in FIG. 9.
Figure 13:
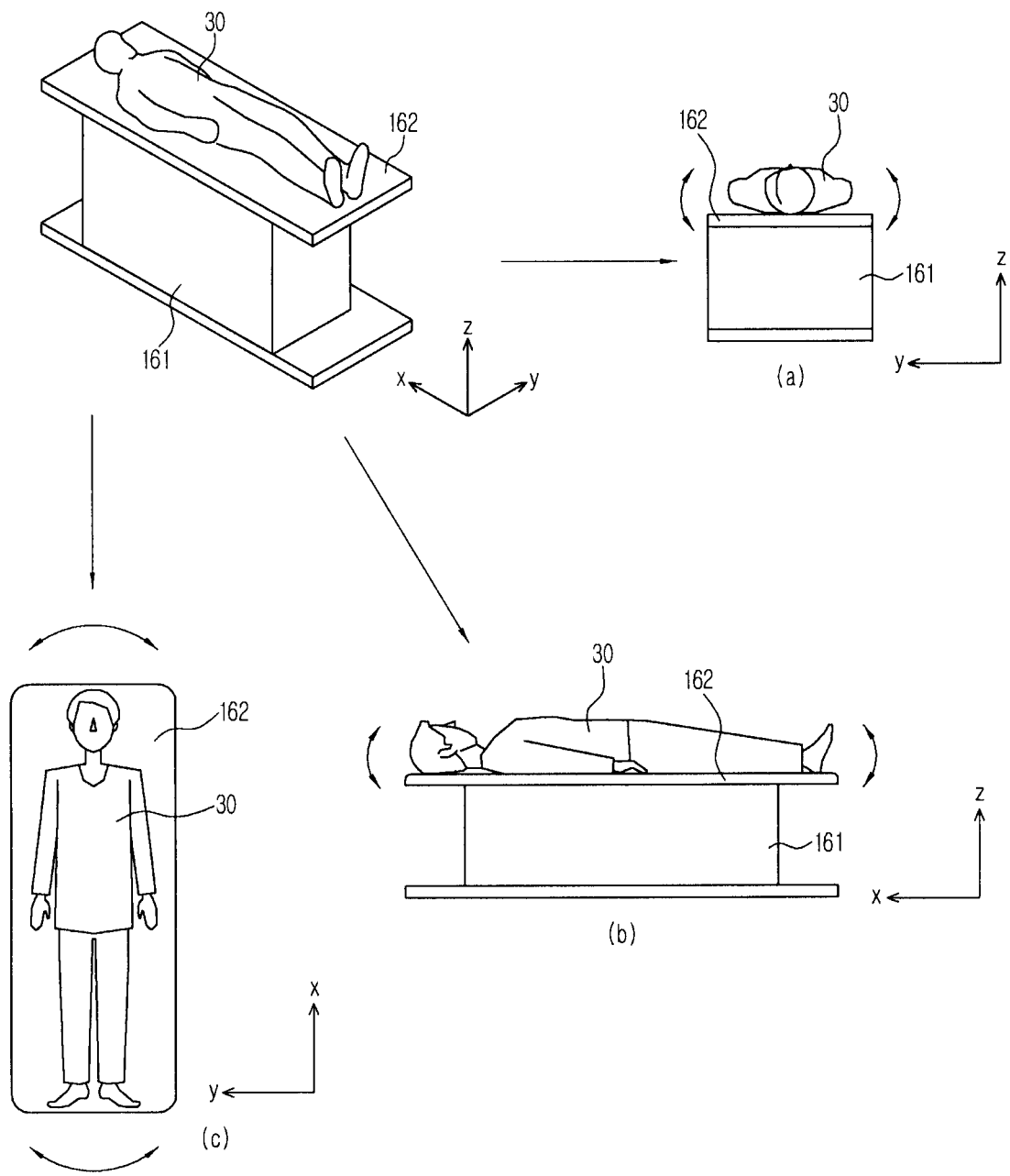
FIG. 13 shows a tiltable cradle of the CT apparatus in accordance with the exemplary embodiment of the present invention.

FIG. 8 shows an example in which a volume image created from the volume data of the subject 30 is divided into a plurality of volumes, FIG. 9 shows the center lines of the individual volumes shown in FIG. 8, and FIG. 10 shows a method of forming the center line of each volume shown in FIG. 9. FIG. 11 shows the center lines of the individual volumes shown in FIG. 9 and the driving axis c of the gantry 103, FIG. 12 shows an example in which one of the center lines of the volumes shown in FIG. 9 has matched the driving axis c of the gantry 103, and FIG. 13 shows the tiltable cradle 162 of the CT apparatus in accordance with the exemplary embodiment of the present invention.

After the controller 141 acquires volume data of the subject 30, as described above with reference to FIGS. 2-7, the controller 141 divides the 3D volume image of the subject 30 created from the volume data of the subject 30 into a plurality of volumes as shown in FIG. 8. In FIG. 8, the respective volumes are represented by $V_0$ through $V_6$, which may be irregularly shaped. That is, the present invention may have the thicknesses or widths of the volumes $V_0$ through $V_6$ be irregular or non-uniform, such that relevant portions of the subject 30 are imaged at the same time. Alternatively, the thicknesses or widths of the volumes $V_0$ through $V_6$ may be uniform or constant.

The volumes may be divided based on a body's main parts. For example, as shown in FIG. 8, the volumes may be divided into head, breast, and abdomen. In particular, the volume $V_0$ may correspond to the brain or other portions of the upper cranium; the volume $V_1$ may correspond to the mouth and/or the throat; the volume $V_2$ may correspond to the upper arms, heart, lungs, chest, and breast region; the volume $V_3$ may correspond to the lower arms, hands, torso, and/or the abdominal region; the volume $V_4$ may correspond to the lower abdominal and genital region; the volume $V_5$ may correspond to the knees and surrounding knee joint regions; and the volume $V_6$ may correspond to the lower leg and feet regions. However, the volume image may be more roughly or finely divided.

If the volume image is divided as shown in FIG. 8, the controller 141 calculates the center lines of the divided volumes. In FIG. 9, the center lines of the respective volumes are represented by $L_0$ through $L_6$ in correspondence with $V_0$ through $V_6$, respectively.

The center line of each volume may be formed by connecting the center points of individual slices to each other. In FIG. 10, slices constituting the volume $V_2$ among the volumes $V_0$ through $V_6$ shown in FIG. 8 are represented by $V_{2,1}$ through $V_{2,n}$. As shown in FIG. 10, the center line $L_2$ of the volume $V_2$ is formed by connecting the center points of the slices to each other.

Since the shapes or areas of slices constituting the individual volumes may be different from each other, as shown in FIG. 9, the center lines of the individual volumes may have different gradients.

FIG. 11 shows the volume image of the subject 30 shown in FIG. 10 and the driving axis c of the gantry 103, which would be a central axis parallel to the longitudinal axis of the bore 105, with the driving axis c extending out of the page of FIG. 6, being perpendicular to the view of the bore 105 shown in FIG. 6.

For example, when the head of the subject 30 is scanned, as shown in FIG. 11, the driving axis c of the gantry 103 does not match the center line $L_0$ of the volume $V_0$ corresponding to the head of the subject 30.

As described above, since the CTDI of X-rays with respect to the subject 30 significantly increases as the center line of the subject 30 increasingly deviates from the driving axis c of the gantry 103, the subject 30 may be exposed to a high dose of X-rays if the subject 30 is scanned in the state in which the driving axis c of the gantry 103 does not match the center line of the subject 30 as shown in FIG. 11.

FIG. 12 shows an example in which the center line of the head (that is, a part to be scanned) of the subject 30 has been matched the driving axis c of the gantry 103.

That is, for example, when the head of the subject 30 is scanned, as shown in FIG. 12, the center line $L_0$ of the volume $V_0$ corresponding to the head of the subject 30 moves to match the driving axis c of the gantry 103.

In order to cause the center line $L_0$ of the subject 30 to match the driving axis c of the gantry 103, as shown in FIG. 12, the position of the subject 30 has to be adjusted such that the feet of the subject 30 are positioned higher than the head of the subject 30, and overall the body of the subject 30 is tilted by an appropriate angle.

In the exemplary embodiment of the present invention, the position of the cradle 162 is adjusted as shown in FIG. 12, such that the center line $L_0$ of the volume $V_0$ matches the driving axis c of the gantry 103 for scanning the volume $V_0$. Subsequent scanning of each volume is performed in a similar manner, such that the center line $L_1$ of the volume $V_1$ is matched with the driving axis c of the gantry 103 for scanning the volume $V_1$, the center line $L_2$ of the volume $V_2$ is matched with the driving axis c of the gantry 103 for scanning the volume $V_2$, etc.

FIG. 13 shows examples of the various directions in which the cradle 162 is tilted.

As shown in (a) of FIG. 13, both lateral sides of the cradle 162 which are parallel to the x-axis may be tilted in the up and down direction to roll the cradle 162 and the subject 30, and as shown in (b) of FIG. 13, both longitudinal ends of the cradle 162 parallel to the y-axis may also be tilted in the up and down direction to pitch the cradle 162 and the subject 30. Also, as shown in (c) of FIG. 13, the cradle 162 may be rotated on the xy plane in a clockwise direction or in a counterclockwise direction to yaw the cradle 162 and the subject 30 about the z-axis.

Also, the operations shown in (a), (b), and (c) of FIG. 13 may be combined to more finely adjust the position of the cradle 162. The tilting of the cradle 162 in the various directions shown in FIGS. 12-13 may be implemented using a plurality of motors in a manner known in the art, which are controlled by the controller 141.

When the center line of a volume including a scan zone is calculated, the controller 141 recognizes a difference in position between the center line of the volume and the driving axis c of the gantry 103, calculates to what degree the position of the cradle 162 has to be adjusted in order to cause the center line of the volume to match the driving axis c of the gantry 103, based on the recognized difference in position, and controls the driver 130 according to the calculated degree.

The driver 130 adjusts the position of the cradle 162 according to a control command of the controller 141 such that the center line of a volume including a scan zone matches the driving axis of the gantry 103.

The controller 141 creates volume data of the subject 30 from images of the subject 30 photographed by the camera 115 as described in connection with FIG. 3 or 6, and when the volume data of the subject 30 is created, the controller 141 calculates an optimum dose of X-rays based on the volume data in a manner known in the art, using known techniques for determining the optimum dose based on the volume data. The subject 30 is then scanned with the calculated optimum dose of X-rays. At this time, in order to reduce the CTDI of X-rays, the subject 30 is scanned in the state in which the center line of a volume including a scan zone among volumes constituting the subject 30 matches the driving axis c of the gantry 103, by repeatedly tilting the cradle 162 and the subject 30 as shown in FIG. 12 for each of the volumes $V_0$ through $V_6$, and scanning each volume with the respective calculated dose of X-rays upon matching the driving axis c.

Figure 14:
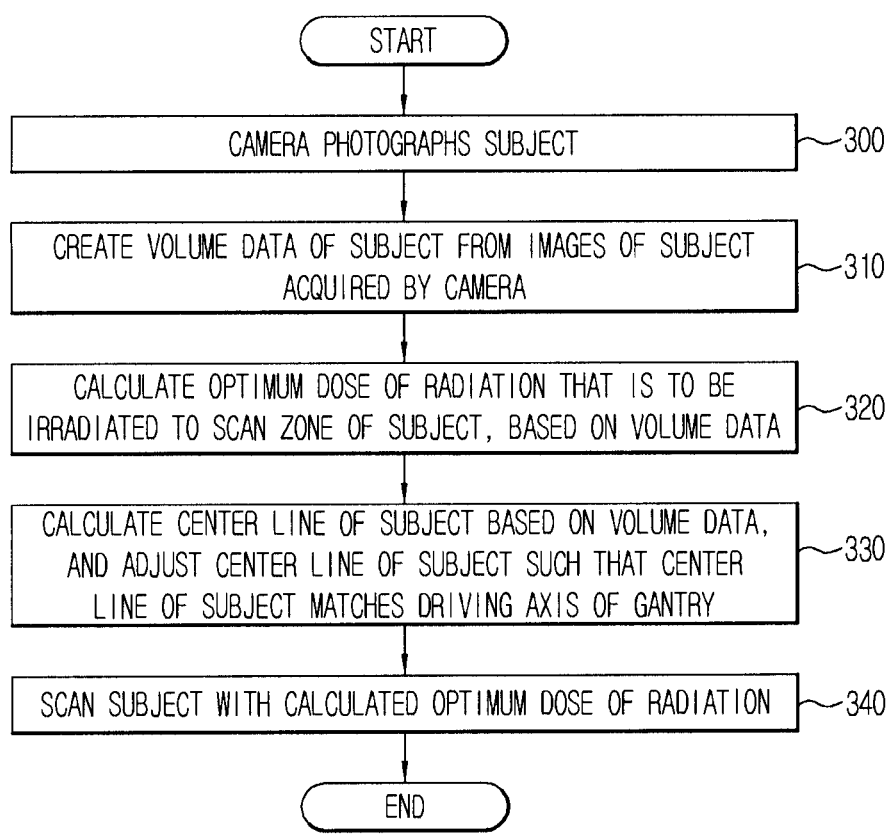
FIG. 14 is a flowchart showing a control method of the CT apparatus, in accordance with the exemplary embodiment of the present invention.

FIG. 14 is a flowchart showing a control method of a CT apparatus, in accordance with the exemplary embodiment of the present invention.

Referring to FIGS. 1-14, the camera 115 photographs the subject 30 in step 300, as shown in FIGS. 3-6. Then the controller 141 creates the volume data of the subject 30 in step 310, as shown in FIGS. 7-8. The controller 141 calculates an optimum dose of X-rays that are to be irradiated to a scan zone of the subject 30, based on the volume data of the subject 30 in step 320, and optionally displays the optimum dose on the display 142 in FIG. 1. The controller 141 then calculates the center line of the subject 30 based on the volume data, as shown in FIGS. 9-11, and causes the center line of the subject 30 to match the driving axis c of the gantry 103 as shown in FIGS. 12-13 in step 330. Each time that the controller 142 causes the center line of the subject 30 to match the driving axis c of the gantry 103 as shown in FIGS. 12-13, the controller 141 scans each divided volume of the subject 30 with the calculated optimum dose of X-rays of the corresponding divided volume, generates a scanned image for the subject 30 and/or the divided volume of the subject 30, and displays the scanned image on the display 142 in step 340. The method of FIG. 14 then ends.

The above-described apparatus and methods according to the present invention can be implemented in hardware or firmware, or via the execution of software or computer code, or combinations thereof. Various components such as a controller, a central processing unit (CPU), a processor, and any unit or device described herein includes at least hardware and/or other physical structures and elements. In addition, the software or computer code can also be stored in a non-transitory recording medium such as a CD ROM, a RAM, a ROM whether erasable or rewritable or not, a floppy disk, CDs, DVDs, memory chips, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software, computer code, software modules, software objects, instructions, applications, applets, apps, etc. that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include volatile and/or non-volatile storage and memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, the program may be electronically transferred through any medium such as communication signals transmitted by wire/wireless connections, and their equivalents. The programs and computer readable recording medium can also be distributed in network-coupled computer systems so that the computer readable code is stored and executed in a distributed fashion.

Although a few exemplary embodiments of the present invention have been shown and described, it would be appreciated by those skilled in the art that changes may be made in these exemplary embodiments without departing from the principles and spirit of the invention, the scope of which is defined in the claims and their equivalents.

What is claimed is:

1. A radiation imaging apparatus comprising:
a gantry;
a camera installed on the gantry, and configured to photograph a subject;
a radiation emitter;
a display; and
a controller for controlling the camera to photograph the subject at multiple angles, to create volume data from images of the subject acquired by the camera, to calculate a dose of radiation that is to be irradiated to a scan zone of the subject based on the volume data of the subject, to control the radiation emitter to scanning the subject with the calculated dose of radiation, to generate a scanned image of the subject, and to control the display to display the scanned image of the subject.

2. The radiation imaging apparatus according to claim 1, further comprising a controller configured to rotate the gantry, and to drive the camera to photograph the subject while the gantry rotates.

3. The radiation imaging apparatus according to claim 2, wherein the controller controls driving of the camera to photograph the subject at predetermined regular time intervals while the gantry rotates.

4. The radiation imaging apparatus according to claim 2, wherein the controller controls driving of the camera to photograph the subject at predetermined regular angles while the gantry rotates.

5. The radiation imaging apparatus according to claim 2, wherein the controller creates volume data of the subject from photographed images of the subject acquired from the camera while the gantry rotates.

6. The radiation imaging apparatus according to claim 5, wherein the controller calculates the dose of radiation based on volume data of a scan zone of the subject.

7. The radiation imaging apparatus according to claim 5, wherein the controller divides a volume of the subject into a plurality of volumes in a direction perpendicular to a driving axis of the gantry, obtains a center line of each divided volume, and adjusts a position of the center line of each divided volume including a scan zone of the subject such that the center line of each divided volume matches the driving axis of the gantry.

8. The radiation imaging apparatus according to claim 7, wherein the controller obtains the center line of each divided volume by connecting center points of slices constituting each divided volume to each other.

9. The radiation imaging apparatus according to claim 7, further comprising a tiltable cradle upon which the subject is disposed, wherein the controller adjusts tilting of the cradle such that the center line of each divided volume including the scan zone of the subject matches the driving axis of the gantry.

10. The radiation imaging apparatus according to claim 1, wherein the camera includes a plurality of cameras are installed on the gantry at predetermined regular distance intervals.

11. The radiation imaging apparatus according to claim 10, further comprising a controller configured to create volume data of the subject from images of the subject acquired by the plurality of cameras.

12. The radiation imaging apparatus according to claim 1, wherein the camera includes an infrared camera.

13. A control method of a radiation imaging apparatus, comprising:
- photographing a subject using a camera installed on a gantry;
- creating volume data of the subject from images of the subject acquired by the camera;
- calculating a dose of radiation that is to be irradiated to a scan zone of the subject, based on the volume data of the subject;
- scanning the subject with the calculated dose of radiation;
- generating a scanned image of the subject; and
- displaying the scanned image of the subject on a display.

14. The control method according to claim 13, wherein the photographing of the subject comprises:
- rotating the gantry; and
- driving the camera to photograph the subject while the gantry rotates.

15. The control method according to claim 14, wherein the driving of the camera to photograph the subject while the gantry rotates comprises controlling driving of the camera to photograph the subject at predetermined time intervals while the gantry rotates.

16. The control method according to claim 14, wherein the driving of the camera to photograph the subject while the gantry rotates comprises controlling driving of the camera to photograph the subject at predetermined angles while the gantry rotates.

17. The control method according to claim 13, wherein the calculating of the dose of radiation that is to be irradiated to the scan zone of the subject, based on the volume data of the subject, comprises:
- dividing the volume of the subject into a plurality of volumes;
- obtaining a center line of each divided volume;
- adjusting a position of the center line of each divided volume including the scan zone of the subject such that the center line of each divided volume matches a driving axis of the gantry; and
- calculating the dose of radiation based on each divided volume including the scan zone of the subject.

18. The control method according to claim 17, wherein the dividing of the volume of the subject into the plurality of volumes comprises dividing the volume of the subject into the plurality of volumes in a direction perpendicular to the driving axis of the gantry.

19. The control method according to claim 17, wherein the obtaining of the center line of each divided volume comprises:
- obtaining center points of slices constituting each divided volume; and
- obtaining the center line of each divided volume by connecting the center points of the slices to each other.

20. The control method according to claim 17, wherein the adjusting of the position of the center line of each divided volume including the scan zone of the subject such that the center line of each divided volume matches the driving axis of the gantry comprises adjusting tilting of a tiltable cradle on which the subject is positioned such that the center line of each divided volume including the scan zone of the subject matches the driving axis of the gantry.

* * * * *